(12) United States Patent
Evans et al.

(10) Patent No.: US 8,399,838 B2
(45) Date of Patent: Mar. 19, 2013

(54) TERAHERTZ INVESTIGATIVE SYSTEM AND METHOD

(75) Inventors: Michael John Evans, Cambridge (GB); Ian Stephen Gregory, Cambridge (GB); Hideaki Page, Cambridge (GB)

(73) Assignee: TeraView Limited, Cambridge (GB)

( * ) Notice: Subject to any disclaimer, the term of this patent is extended or adjusted under 35 U.S.C. 154(b) by 47 days.

(21) Appl. No.: 12/358,877

(22) Filed: Jan. 23, 2009

(65) Prior Publication Data

US 2009/0314944 A1   Dec. 24, 2009

(30) Foreign Application Priority Data

Jan. 24, 2008   (GB) .................................. 0801318.7

(51) Int. Cl.
    *G01J 5/02*   (2006.01)
(52) U.S. Cl. ............... 250/341.8; 250/341.2; 250/336.1; 250/559.01; 250/559.07; 250/559.08; 250/234
(58) Field of Classification Search ............... 250/341.8, 250/341.2, 336.1, 559.01, 559.07, 559.08, 250/234
    See application file for complete search history.

(56) References Cited

U.S. PATENT DOCUMENTS

| | | | | |
|---|---|---|---|---|
| 3,794,161 A * | 2/1974 | Peterson | ................... | 209/540 |
| 3,956,329 A * | 5/1976 | Murakami et al. | ............ | 544/352 |
| 4,281,765 A * | 8/1981 | Brazell et al. | ................. | 209/576 |
| 4,420,261 A * | 12/1983 | Barlow et al. | ................. | 356/621 |
| 4,691,231 A * | 9/1987 | Fitzmorris et al. | ............ | 348/127 |
| 4,868,901 A * | 9/1989 | Kniskern et al. | ............ | 250/222.2 |
| 4,972,494 A * | 11/1990 | White et al. | ................... | 382/143 |
| 5,357,441 A * | 10/1994 | Petty et al. | ..................... | 702/104 |
| 6,272,440 B1 * | 8/2001 | Shakespeare et al. | .......... | 702/85 |
| 6,316,772 B1 * | 11/2001 | Egelberg | ................. | 250/339.11 |
| 6,975,408 B2 * | 12/2005 | Igaki et al. | ..................... | 356/616 |
| 7,878,391 B2 * | 2/2011 | Kalkhoff | ..................... | 235/98 C |
| 2002/0071121 A1 * | 6/2002 | Ortyn et al. | ..................... | 356/419 |
| 2005/0104017 A1 * | 5/2005 | Kimba et al. | ............ | 250/559.07 |
| 2006/0056586 A1 * | 3/2006 | Uetake et al. | ................... | 378/57 |
| 2007/0257216 A1 * | 11/2007 | Withers et al. | ................ | 250/580 |
| 2007/0272841 A1 * | 11/2007 | Wiklof | .......................... | 250/234 |
| 2009/0123060 A1 * | 5/2009 | Liu et al. | ...................... | 382/149 |
| 2009/0153838 A1 * | 6/2009 | Vugts et al. | ..................... | 356/51 |

FOREIGN PATENT DOCUMENTS

| | | |
|---|---|---|
| GB | 2 347 835 A | 9/2000 |
| GB | 2 399 626 A | 9/2004 |
| GB | 2 405 466 A | 3/2005 |
| GB | 2 446 026 A | 7/2008 |
| WO | WO 87/01976 A1 | 4/1987 |
| WO | WO 2005/119214 A1 | 12/2005 |
| WO | WO 2006/085904 A3 | 8/2006 |
| WO | WO 2006092557 A1 * | 9/2006 |
| WO | WO 2008/001785 A1 | 1/2008 |
| WO | WO 2008/122597 A1 | 10/2008 |

\* cited by examiner

*Primary Examiner* — David Porta
*Assistant Examiner* — Djura Malevic
(74) *Attorney, Agent, or Firm* — Dickstein Shapiro LLP

(57) ABSTRACT

A system for investigating a plurality of samples having varying positions or orientations moving with respect to the system, the system including an emitter of terahertz radiation for irradiating a sample provided in a sample space; a detector of terahertz radiation configured to detect radiation reflected from said sample space; and determining means to determine if radiation reflected from said sample space is from a sample with a predetermined orientation in the sample space.

12 Claims, 10 Drawing Sheets

TERAHERTZ INVESTIGATIVE SYSTEM AND METHOD

BACKGROUND OF THE INVENTION

The present invention relates to the field of measuring samples using Terahertz radiation. More specifically, the present invention relates to measuring samples which have an orientation which is not controlled for a Terahertz measurement.

THz radiation has been employed to measure and characterise many different materials such as pharmaceutical products, coating layers, paint, chemicals etc. Terahertz technology allows for the first non-destructive imaging of chemical and/or structural features of the pharmaceutical tablet containing the active pharmaceutical ingredient (API) and excipients (fillers).

Typically a THz beam is launched at the sample and either the reflected or transmitted beam is analysed to yield pertinent metrics about the sample. Many important materials are transparent to THz radiation and have important characteristic spectral features in the THz frequency range. Therefore the internal structure and chemical composition of the sample may be measured.

These measurements are usually conducted with the sample held stationary in a well defined orientation. This is to optimise the collected radiation for maximum quality of signal. This is because the THz specular reflectance of many interesting materials is relatively low <10% and the diffuse reflectance is ~three orders of magnitude below the specular reflectance. The situation is further complicated by the relatively weak signals that are produced and detected by THz devices. Often a well orientated stationary sample is needed to produce any signal at all. Furthermore, weak signals need to be averaged over a time that is longer than the tablet motion.

An example of an application of THz technology is to generate non-destructive images of internal structures within pharmaceutical solid dosage products. One of these internal structures is the outer coating of the product, designed for a number of different functions; cosmetic, control release of the active ingredient and protection of the active ingredient from the atmosphere. The uniformity of the coating can critically affect the bio availability (rate of absorption of a drug by the body and therapeutic efficacy of the accompanying dosage form) to patients. Process control during the coating stage is thus critical, but is currently limited to remote analysis.

One proven approach utilises the current Terahertz Pulsed Imaging (TPI) technology, which uses a 'time-delay' sampling technique to measure the information contained within the pulse shape itself, and not just the reflected power. Another approach utilises the current Terahertz Pulsed Imaging (TPI) technology 'time-delay' sampling technique to measure the peak amplitude of the reflected THz pulse.

In all of these examples a well defined special relationship between the THz pulse (i.e. that delivered by the THz optics) and the sample position is required. The rate at which a spectra or image may be obtained is thus limited by the mechanical arrangement of the delivery system—for example a motorised stage or a robotic handling arm.

However, many industrial processes produce large numbers of continuously moving, rotating and randomly orientated samples. These measurement scenarios present a challenge for sample measurement using THz radiation as the position, orientation and velocity of the sample cannot be guaranteed during the measurement time. The data collected is usually confused with the added parameters of the sample motion, position and orientation.

SUMMARY OF THE INVENTION

The present invention at least partially addresses the above problems and allows good THz signals to be acquired from rapidly moving samples which do not have a fixed orientation or an orientation which can be controlled by the THz investigating system itself.

Thus, in a first aspect, the present invention provides a system for investigating a plurality of samples having varying positions or orientations moving with respect to said system, the system comprising:

an emitter of terahertz radiation for irradiating a sample provided in a sample space;

a detector of terahertz radiation configured to detect radiation reflected from said sample space; and determining means to determine if radiation reflected from said sample space is from a sample with a predetermined orientation in said sample space.

If samples which do not have a fixed orientation and/or fixed exact position are made to pass through the sample space by some external mechanism, the motion of the samples through the sample space means that there is a finite probability that one sample will have the correct orientation to allow the THz signal from the emitter to be coupled to the THz detector.

The determining means allows the system to determine if data has been received from a sample which has the correct orientation in the sample space when the measurement is performed. Since many samples will be curved the exact position of the sample as well as its orientation may be a factor.

The determining means may be provided by software or physical means such as electronic components or optical means.

In a preferred embodiment, the determining means comprise optics configured to reduce the number of signals from reaching the detector which are not from a sample with said predetermined orientation in said sample space. For example, the determining means may comprise con-focal optics.

In addition to or as an alternative to using optics to filter out unwanted signals, the determining means comprises means for comparing received detector signals with a threshold. For example, said received detector signal may be compared with a threshold by comparing the height of the received pulse with a threshold value for the height of the received pulse. The height of the received pulse may be the maximum height of the received pulse, the height of a pulse within a narrow time window or the height of a pulse with a pulse width below a maximum value.

The comparison of signals with a threshold may take place during acquisition of a signal or the system may further comprising memory means configured to store received detector signals and said determining means are configured to sift through said signals in said memory means.

The system may be provided as a quality control system as it will be able to sample a fraction of all tablets passing through the system. The system may comprise means to record statistics on the number of tablets which have passed through the system and the number of valid readings (i.e. the readings where a sample is in the correct orientation and position). The system may also be configured to record statistics on the number of valid readings and the number of invalid readings.

The system may be adapted to fit to a conveyor belt, chute or container configured to move said samples with respect to said sample space. The system may also comprise a conveyor belt, chute or container.

Thus, in a second aspect, the present invention provides a system for investigating a plurality of samples having varying positions or orientations moving with respect to said system, the system comprising:

an emitter of terahertz radiation for irradiating a sample provided in a sample space;

a detector of terahertz radiation configured to detect radiation reflected from said sample space; and delivery means configured to move said samples with respect to said sample space, wherein said delivery means does not control the orientation or the exact position of the samples.

In pharmaceutical applications, the system may be adapted to look at either in-line examination of tablets or other solid dosage forms during production, or on-line applications where a portion of the samples are randomly sampled off the production line. Different points in the tablet production stages could be used to inspect pharmaceutical products—within coating pans, dryers, at the output of tablet presses etc.

Thus, in a third aspect, the present invention provides a production line comprising:

manufacturing means comprising a plurality of stages for producing samples, delivery means for moving samples to and from said stages; and a system according to either the first or second aspects, coupled to said line for investigating samples moving on said delivery means.

Previously, the system has been described with a single emitter and a single detector. However, the system may comprise a plurality of detectors configured to detect radiation from the sample space. Also, the system may comprise a plurality of emitters. A single detector may be provided for each emitter or a plurality of detectors may be provided for each emitter.

The system may comprise an array of emitters and detectors such that multiple measurements may be made across the width of a conveyor belt, chute, container or the like.

It is also possible for the samples to be fixed and for the system to move. For example, the system may be a handheld scanner or the like which can be passed over a container of tablets etc.

The system is preferably configured so that the detector performs the measurement in a time scale faster than the sample motion such that the sample may be considered to be quasi-stationary. For example, the detector performs the measurement in a time scale such that the sample motion introduces an error of 10% or less in the measurement, more preferably 5% or less, even more preferably 3% or less.

The system may be used to perform a number of investigative measurements on a number of different types of samples. For example, in the pharmaceutical field, the system can be used to produce data to determine:

Coating thickness and uniformity on tablets
Coating density and uniformity on tablets
Content (active ingredient) amount and uniformity in tablets
Density of layers inside tablets
Core integrity
Delamination and capping of tablets
Stability characteristics of tablets—eg water ingression
Content uniformity and amount of materials in capsules
Distribution of active ingredients and excipients in tablets
Dissolution or bioavailability characteristics of solid dosage forms However, the present invention is not limited to the pharmaceutical field and may also be used for:

Paint thickness, uniformity and contaminants/corrosion on car, aircraft and ship bodies
Composite material inspection on aircraft
Postal and packaging inspection
Food stuff and food product inspection For larger scale items such as car and aircraft bodies, panels and components are produced on automatic production lines and are moved on conveyor belts, containers or the like between production stages. The precise orientation of the panels will not be controlled and thus similar issues are encountered for large area objects such as these as for pharmaceutical samples.

To determine the above quantities, the following THz measurements may be performed: the time between reflections may be used to determine the thickness of layers, distances between interfaces etc which may in turn be combined with weight data to determine density, frequency measurements allow the composition of a sample at different points to be estimated and the presence of impurities to be identified, attenuation of the time domain or frequency domain signal can be used to determine the absorption coefficients and refractive index measurements. This data can be used to indicate more complex quantities such as core integrity, delamination and capping of tablets, stability characteristics of tablets (e.g. water ingression), content uniformity and amount of materials in capsules and dissolution or bioavailability characteristics of solid dosage forms.

In a fourth aspect, the present invention provides a method for investigating a plurality of samples having varying positions or orientations moving with respect to said system, the method comprising:

irradiating a sample provided in a sample space;
detecting radiation reflected from said sample space; and
determining if radiation reflected from said sample space is from a sample with a predetermined orientation in said sample space.

In a fifth aspect, the present invention provides a method for investigating a plurality of samples having varying positions or orientations moving with respect to said system, the method comprising:

irradiating a sample provided in a sample space;
detecting radiation reflected from said sample space; and
delivering said samples such that said samples move with respect to said sample space without control over their orientation or the exact position.

In a sixth aspect, the present invention provides use of Terahertz radiation for investigating samples on a moving delivery system, where said delivery system does not control the orientation or exact position of the samples.

BRIEF DESCRIPTION OF THE DRAWINGS

The present invention will now be described with reference to the following non-limiting embodiments in which.

DETAILED DESCRIPTION OF THE PREFERRED EMBODIMENTS

Figure 1:
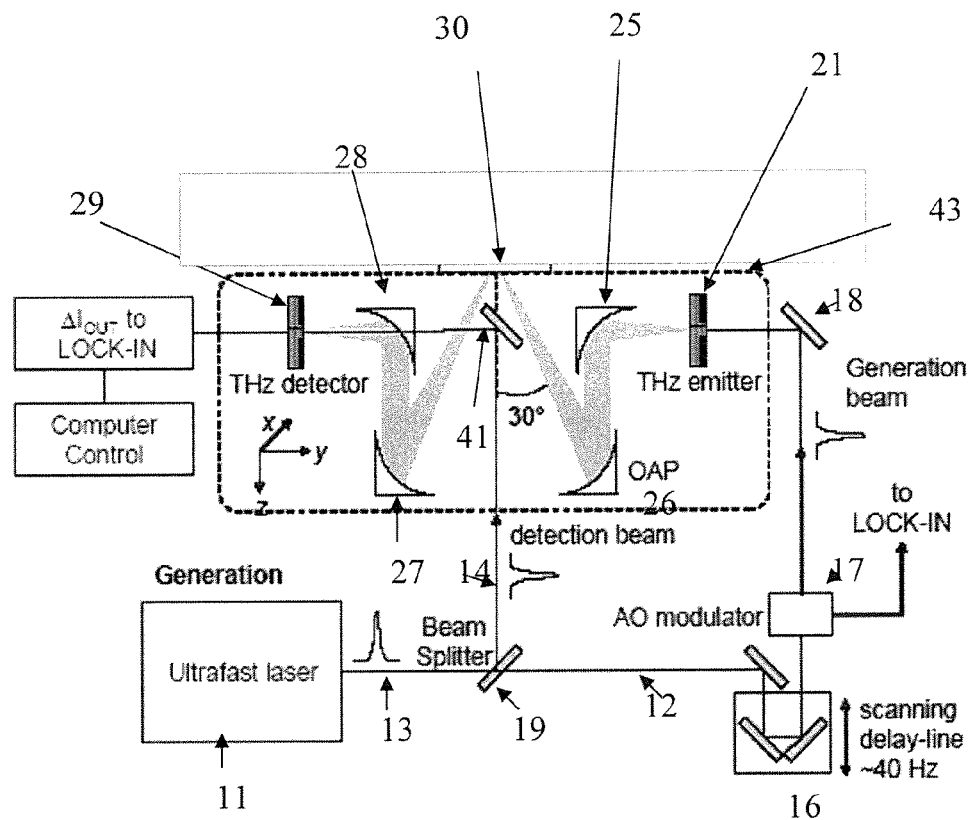
FIG. 1 is a schematic of a terahertz investigative system.

FIG. 1 is a schematic of a terahertz imaging apparatus which may be used to study pharmaceutical tablets. The system shown is a flat bed scanner system. The apparatus comprises an ultra-short pulse laser 11 which may be, for example, Ti:sapphire, Yb:Er doped fibre, Cr:LiSAF, Yb:silica, Nd:YLF, Nd:Glass, Nd:YAG or Alexandrite laser. This laser 11 emits pulses of radiation 13, such as a collimated beam of pulses, each of which comprise a plurality of frequencies. This pulse impinges on beam splitter 19. The beam splitter splits the beam into a pump pulse 12 which is used to irradiate the sample and a probe pulse 14 which is used during detection.

The pump pulse 12 is directed into scanning delay line 16. This delay line is a rapid-scanning type and in its simplest form comprises two mirrors that serve to reflect the beam through a 180° angle. These mirrors are then quickly swept backwards and forwards in order to vary the path length of the pump pulse 12.

The output pump pulse from the scanning delay line 16 is then passed through AO modulator 17 which isolates the laser from reflected light and/or modulates the beam and directed by mirror 18 onto THz source 21. THz source 21 comprises a frequency conversion member and a bow-tie emitter. The frequency conversion member is configured to mix the incident radiation in order to output radiation derived from the differences of the input frequencies, so-called difference frequency generation. This technique is described in more detail in GB 2 347 835.

The emitter 21 abuts a hyper-hemispherical lens (not shown). The terahertz beam that is output from the emitter 21 is directed towards a first parabolic mirror 25. The beam is then reflected off the first parabolic mirror 25 and onto second parabolic mirror 26, which directs the radiation onto a sample which will be placed in sample space 30. The sample may be replaced with a reference sample in order to remove background features from the final results. The radiation which is reflected from sample 30 is then collected by third parabolic mirror 27 and directed onto a fourth parabolic mirror 28. Fourth parabolic mirror has a small aperture. The probe beam 14 is directed via mirror 41 through the aperture of fourth parabolic mirror 28 so that the probe beam can be combined with the radiation which has been reflected by the sample 30.

The combined THz radiation and probe beam then impinge on THz detector 29. In this particular embodiment, the THz detector is a photoconductive detector.

The components from the emitter 21, through the four parabolic mirrors and the detector 29 form the imaging section 43.

The sample introduces a time delay in the path of the pump pulse. The delay is dependent on both the absorption coefficient and the refractive index of the sample. In order to obtain a detection signal, the frequency component of the probe beam must be in phase with a frequency component of the pump beam. Variation of the scanning delay line allows the phase of the probe beam and/or pump beam to be swept with respect to the pump beam and/or probe beam and thus allows for measurement of the delay time of each frequency component which passes through the sample.

This apparatus described can be utilised to obtain time domain data of a sample using broadband phase-sensitive Terahertz radiation.

Figure 2:
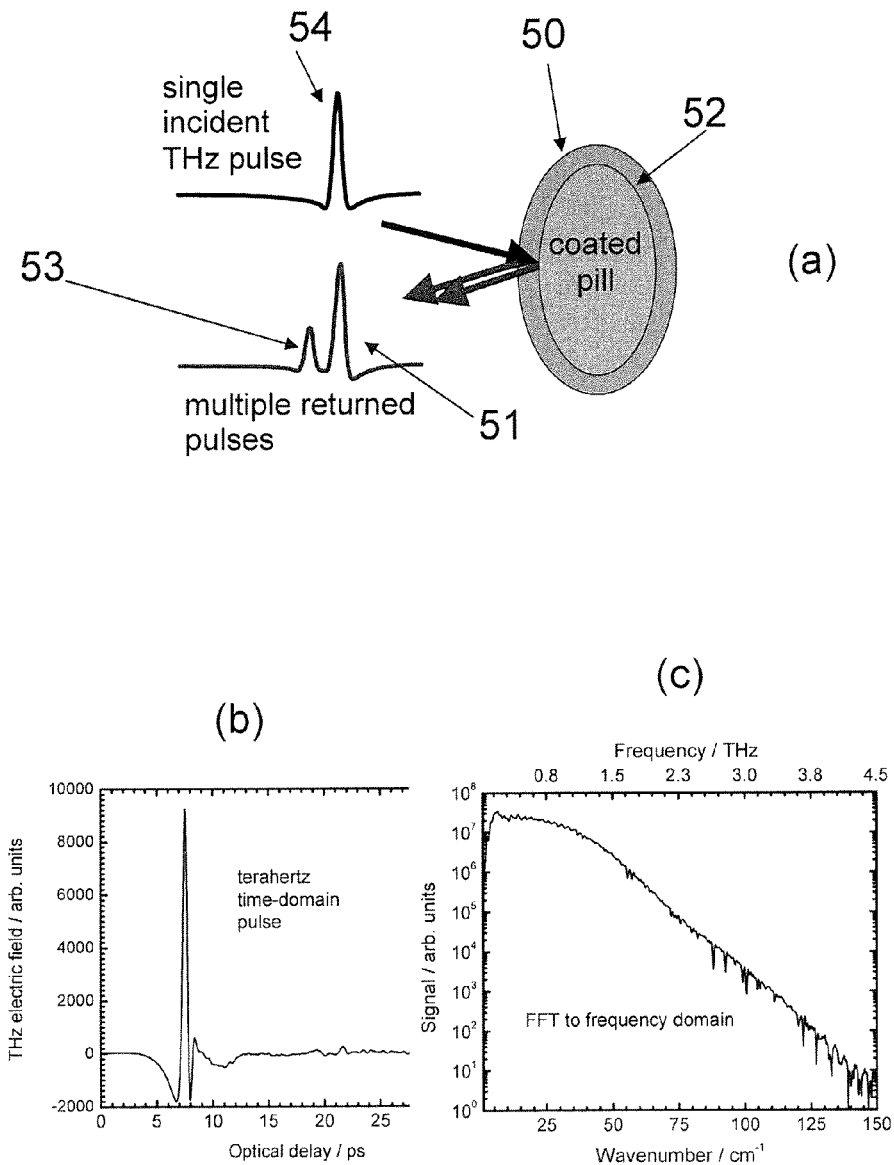
FIG. 2a is a schematic showing the reflection of a THz signal from a tablet.
FIG. 2b is a time domain trace of a THz pulse and FIG. 2c is a frequency domain trace of the pulse of FIG. 2b.

FIG. 2a is a schematic of a tablet with an external surface 50 and an internal interface 52. A pulse of radiation 54 which impinges on the tablet, is first reflected from the external surface 50. This gives rise to large peak 51 in the reflected THz radiation spectra. Radiation which continues through the tablet is reflected from the internal interface 52 giving rise to peak 53 in the THz reflected time domain spectra.

By measuring the time at which the radiation is reflected from the tablet it is possible to associate the measured radiation with different features within the tablet, thus it is possible to measure the thickness of certain layers within the tablet.

FIG. 2b is a time-domain trace of a Terahertz pulse before it is incident on a sample and FIG. 2c is the corresponding frequency domain pulse showing the frequency components which may be extracted from the pulse. The different constituents of a tablet will absorb radiation at different frequencies, thus it is possible to obtain data about the composition of a tablet by studying the frequency response.

Figure 3:
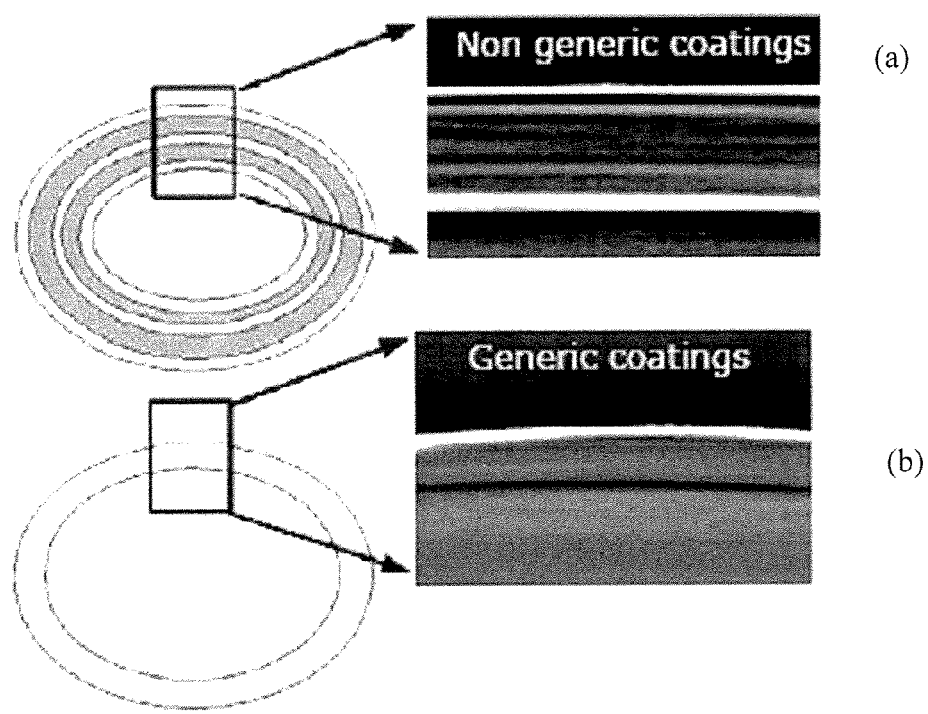
FIG. 3a is a schematic of a pharmaceutical tablet and its corresponding terahertz image and FIG. 3b is a diagram of the coating of a generic version of the pharmaceutical tablet of FIG. 3a and its corresponding terahertz image.

FIG. 3a is a schematic of a tablet with a reasonably complicated coating structure. The corresponding terahertz image of these coatings are shown to indicate the power of the terahertz analysis tool. FIG. 3b is a schematic of a generic form of the tablet of FIG. 3a. The terahertz analysis clearly shows a less complicated coating structure. Therefore, terahertz provides a way of distinguishing between generic and non-generic compounds, or possibly between counterfeit and authentic tablets or solid dosage forms in other contexts.

Figure 4:
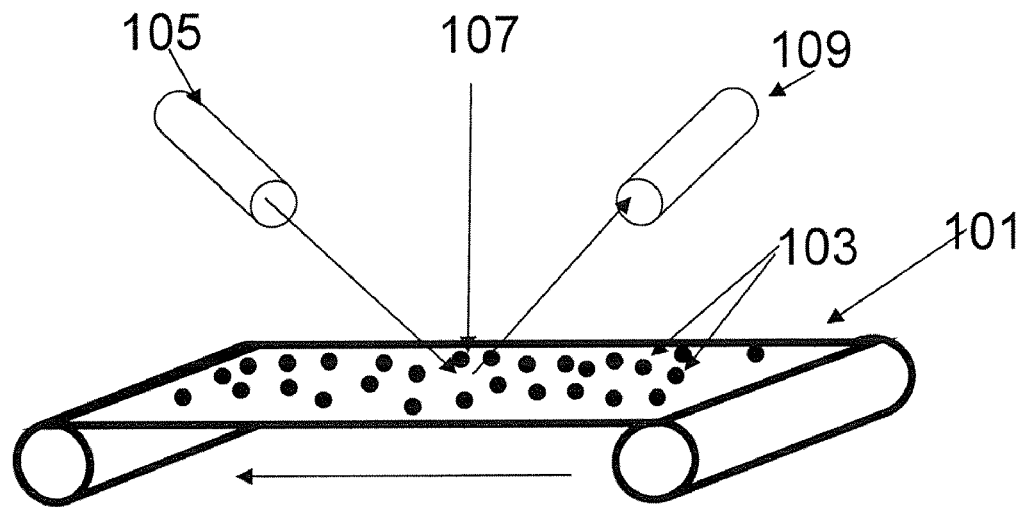
FIG. 4 is a schematic of a system in accordance with an embodiment of the present invention.

FIG. 4 is a schematic of a Terahertz investigative system in accordance with an embodiment of the present invention. The system is coupled to a conveyor belt 101 and tablets 103 are randomly scattered on said conveyor belt 101. The tablets 101 may be delivered to the conveyor belt 101 by a chute or the like so that the tablets are randomly distributed on the belt 101.

A THz emitter 105 provides and focussed a THz beam onto a small area of the conveyor belt 101 which will be termed the sample space 107. A detector 109 is positioned to collect radiation which has been reflected from a tablet 103 in the sample space 107. However, it should be noted that even if a tablet is provided in the sample space 107 when the measurement is performed, due to the curved surface of the tablets 103, the detector 109 will only receive radiation which has been reflected from tablets with a particular surface orientation in the sample space. The system may perform a point measurement or measure a line or area of the sample.

Figure 5:
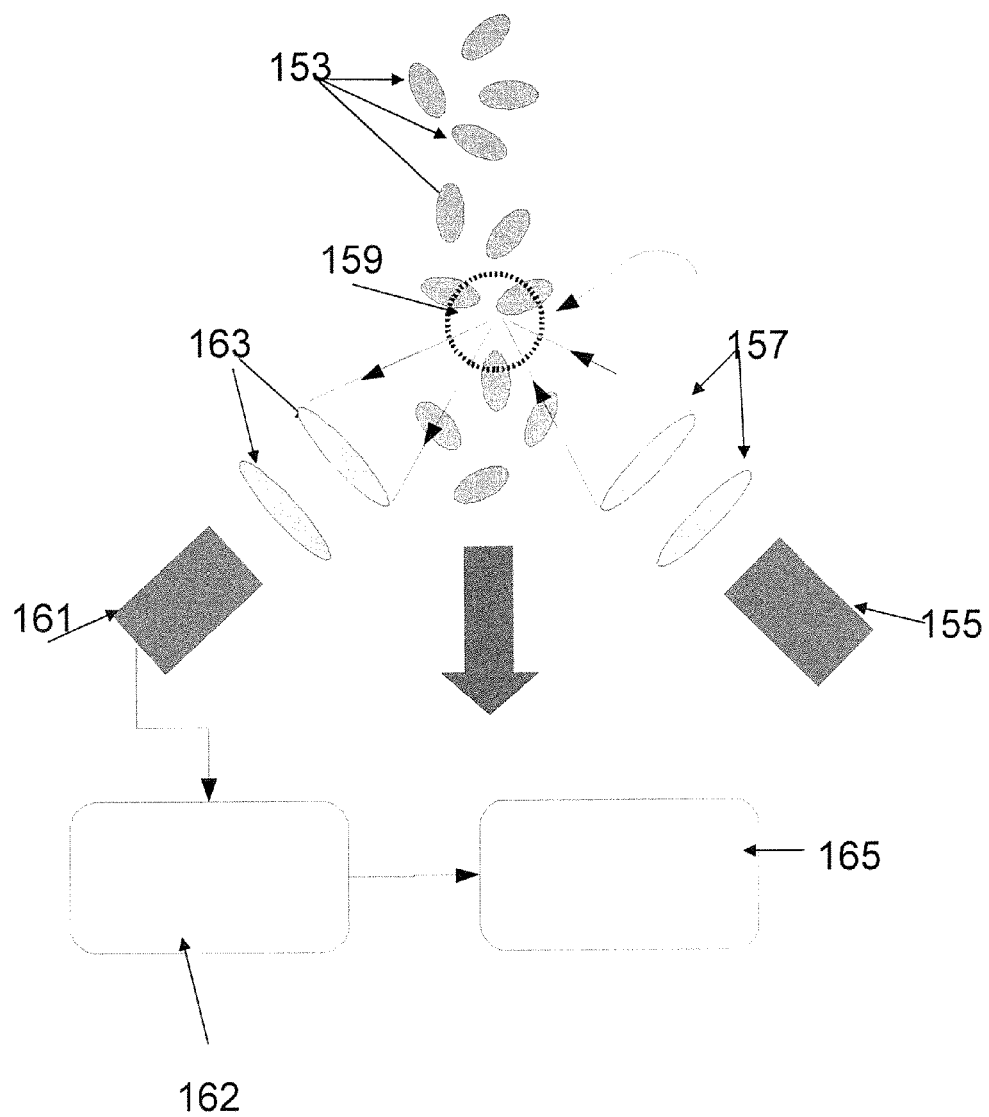
FIG. 5 is a more detailed plan view of the system of FIG. 4.

FIG. 5 shows the system of FIG. 4 in more detail. The samples or tablets 153 are provided on a conveyor belt or the like (not shown). Other mechanisms which may be used are, for example, a tube, chute, container etc An emitter 155 emits a beam of THz radiation which is focussed by emitter optics 157 onto a sample space 159. The THz optics may comprise lenses, mirrors, apertures, or prisms.

A system of THz optics 163 is used to collect the THz radiation from the sample space 159 and direct it onto a THz detector 161. In this embodiment, the measurement is performed within a time scale that is much faster than the sample motion, thus the sample may be considered to be quasi-stationary.

A sample can be considered to be quasi-stationary if the displacement for the sample is small with respect to the displacement of the delay line 16 FIG. 1 over the features of interest. The error in the measurement can be written as $x_{sample}/\Delta x_{delay}$, where $\Delta x_{delay}$ is the displacement of the delay line $x_{sample}$ is the displacement of the sample in this time over the same time. If this ratio is within acceptable limits then the samples can be considered quasi-stationary. This error is related to the scanning frequency of the delay line, f, and its maximum displacement $\Delta x_{max}$ as follows:

$$\frac{x_{sample}}{\Delta x_{delay}} = \frac{v_{sample}}{4\pi f \Delta x_{max}}$$

The sample space 157 is a region in space at the common focal point of the emitter 155 and detector 161 optical systems. The volume of the sample space 157 is defined by the particular system of optics used for the emitter 155 and detector 161.

Randomly orientated samples 153 are made to pass through the sample space 157 by some external mechanism. The random motion of the samples 153 through the sample space 157 means that there is a finite probability that one sample 153 will have the correct orientation to allow the THz signal from the emitter 155 to be coupled to the THz detector 161.

The signal coming from the THz detector 161 passes through signal processing section 162 and into acquisition system 165. In this embodiment, the acquisition system 165 selects data according to the signal passing a threshold condition.

The acquisition system monitors the quality of the received data. Data is only recorded when a threshold of signal quality is passed. The threshold conditions for data quality vary from sample to sample and depend on the information that needs to be measured. For example, if a THz pulse were emitted from the source, the threshold condition could be the height of the received pulse. Therefore only signals with peak heights above the threshold value will be selected. Several threshold metrics may also be applied. For example, peak height, in a well defined time window with a peak width below a critical value. The threshold conditions may be a programmed into the acquisition system depending on the application. The acquisition system provides signal processing functions to improve the quality of data that have passed the measurement thresholds.

This method is general for all THz sources and detectors. For example, photoconductive antennas may be used or a THz laser source and detector.

In an alternative configuration rather than moving the target relative to the THz source and detector, the opposite scheme may be employed. An example may be a hand-held or motorised probe to generate a line scan across a target sample.

Figure 6:
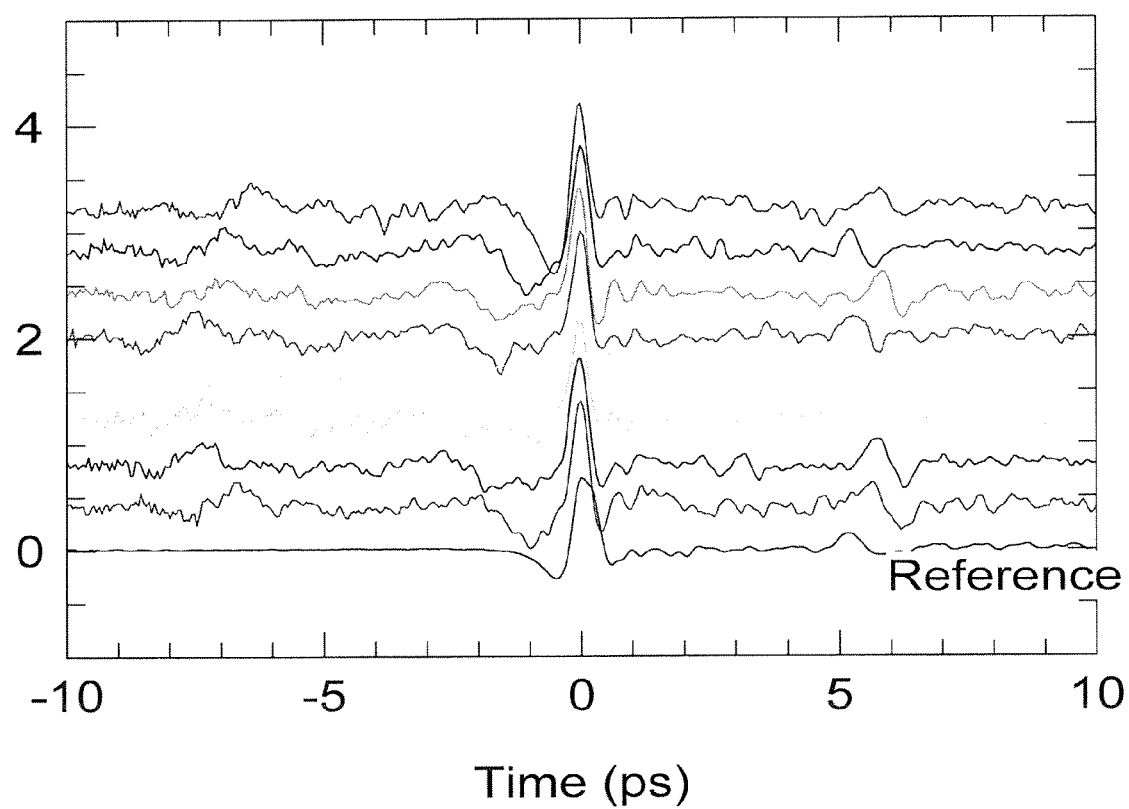
FIG. 6 is a plot of reflected THz pulses collected in the time domain by a system of the type described with reference to FIG. 5.

FIG. 6 is a plot of reflected THz pulses collected in the time domain by a system of the type described with reference to FIG. 5. This data has been sifted by gating against a minimum peak height within a specified time window. The time window required both the main and the second peak (corresponding to the tablet thickness) to be collected. The data was then normalised by setting each of the main peaks to time zero. Due to the motion of the tablet during the measurement, an error of 3% is expected in the data. The second peak is aligned accommodating for this error.

A clear secondary peak may be seen in the order of 5 to 6 ps following the initial t=0 pulse, related to the thickness of the coating later (900 um). These are referenced against a pulse collected from a single placebo tablet from the same batch measured under well defined geometrical conditions.

The above description has concentrated on sifting detected signals by comparing with a threshold. However, it is possible to design optics which will remove such spurious reflections. These may be used in combination with or instead of the mathematical methods described above.

Figure 7:
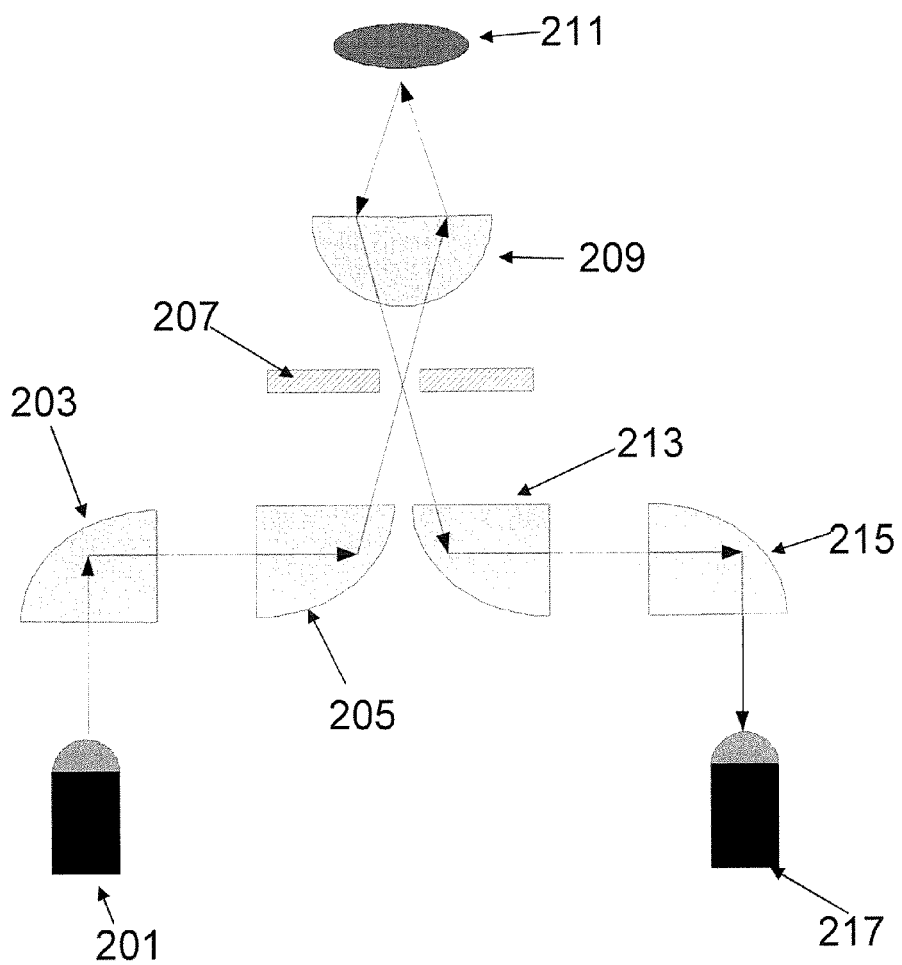
FIG. 7 is a schematic of a THz imaging system in accordance with an embodiment of the present invention having con-focal optics.

FIG. 7 shows an example of a con-focal optical arrangement, which may be used as a way of optically determining between valid and invalid signals. Valid signals being those arising from a sample which passes through the sample space with an orientation sufficient to obtain a signal at the detector which allows a terahertz analysis to be performed.

Terahertz emitter 201 which is of the type previously described emits a terahertz beam to mirror 203, the beam is then reflected from mirror 203 off mirror 205 and through aperture 207. After passing through aperture 207, the beam is focused by lens 209 onto sample 211. If sample 211 is in the correct orientation, the beam will be reflected back and directed by a lens towards mirror 213. A beam travelling from lens 209 to mirror 213 must pass through aperture 207. If the sample 211 is not in the correct orientation, the beam leaving lens 209 will not pass through aperture 207 and instead be blocked. Thus, aperture 207 provides a further method of determining if the signal received from sample is from a sample with a correct orientation.

The beam is then reflected off mirror 213 and mirror 215 into detector 217.

The size of the aperture is preferably bigger than the wavelength required to probe the features of interest in the sample, but small enough to block reflections from non-correctly aligned surfaces from reaching the detector.

The system of FIG. 7 may be used instead of the previously discussed software determining means, electronic filters or it may be used in combination with other determining means.

Previously, the systems which have been discussed have consisted of a single emitter and a single detector. However, it is possible to have multiple emitters and/or multiple detectors.

Figure 8:
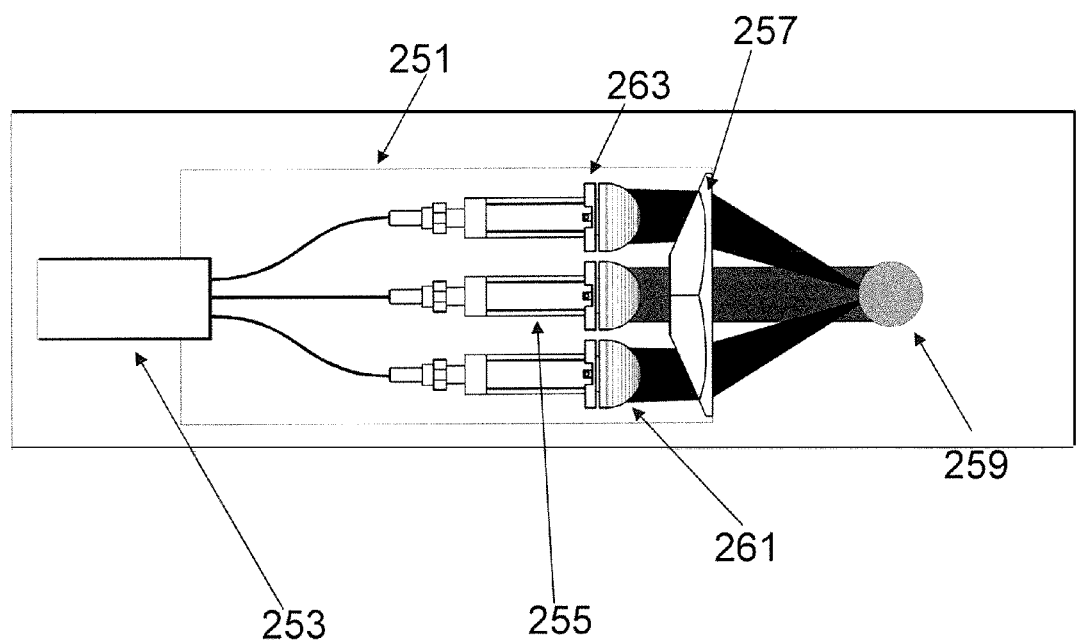
FIG. 8 is a schematic of a system with multiple detectors.

FIG. 8 shows a system which comprises a single emitter 255 which is surrounded by the detectors. As FIG. 8 is a plan view, only two detectors 261 and 263 can be seen in the figure.

The emitter 255 and detectors 261 and 263 are housed in probe housing 251 and signals are delivered to and from the emitters by umbilical 253. The probe housing 251 may be mounted if a fixed head within a system of the type previously described or it may be used as a handheld probe which may be moved in relation to the samples to be tested. For example, the probe may be moved from sample to sample to test multiple samples.

The emitter 255 emits a beam of terahertz radiation which is focused by prism 257 onto sample 259. Sample 259 will reflect radiation. Dependent on its orientation, some of this radiation will be captured by prism 257 and directed into detectors 261 and 263. The signal detected by the detectors 261 and 263 (or any of the other detectors which are not visible in this particular figure) will then be sifted as described with reference to FIG. 4.

Figure 9:
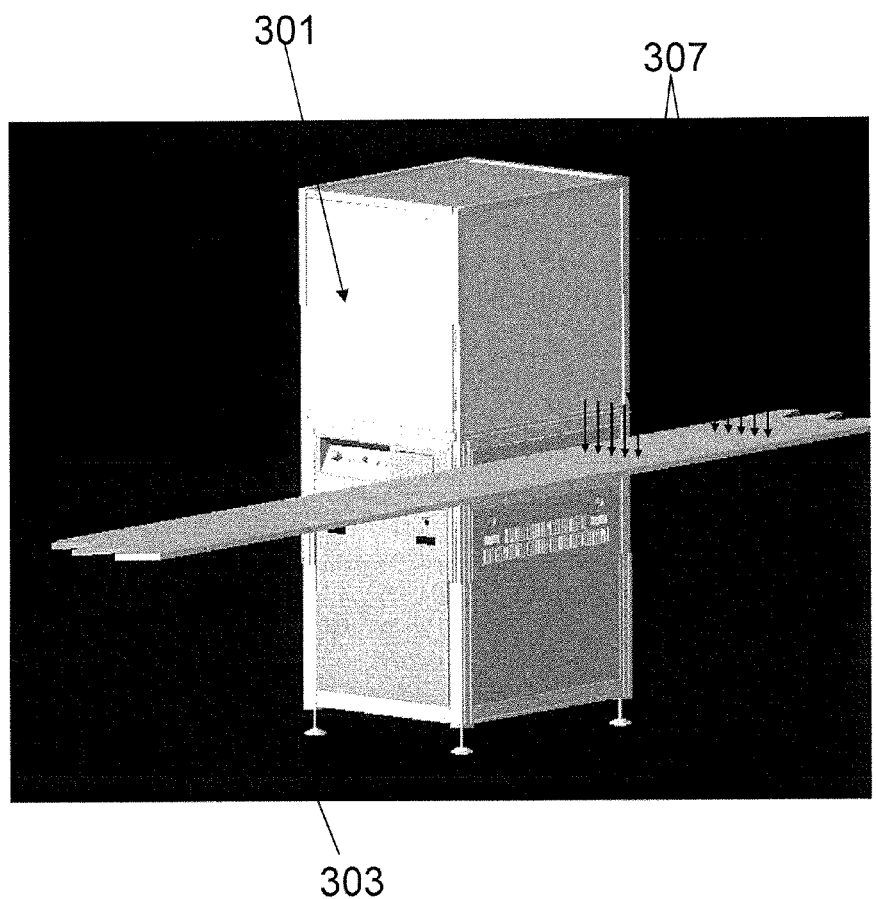
FIG. 9 is a schematic of a system coupled to a pharmaceutical production line.

As previously described, the system may be part of an online production system. FIG. 9 schematically shows how the apparatus may be used in a production line pharmaceutical system for monitoring the quality of tablets. As previously example, the system can be used to determine coating thickness and uniformity on tablets, coating density and uniformity on tablets, content (active ingredient) amounting uniformity in tablets, density of layers inside tablets, core integrity, delamination of and capping of tablets, stability characteristics of tablets e.g. water ingression, content uniformity and amount of materials in capsules, distribution of active ingredients and recipients in tablets and dissolution or bio-availability characteristics of solid dosage forms.

In the system of FIG. 9, a terahertz system is supplied which is of the type described with reference to FIG. 5. The system is provided next to a conveyor belt 301 which carries tablets past the system.

In the system shown in FIG. 9, there are eight probe heads shown by arrows 307 which continually monitor the tablets passing on conveyor belt 301. The probe head 307 may each have a single detector and single emitter or may be of the multiple emitter/detector type for example the type described with reference to FIG. 8. In this example, the emitters and detectors are arranged in two linear arrays.

In FIG. 9, the terahertz system is shown as being a separate stage in the production line. However, the terahertz system may be incorporated at any stage in the production, for example after the tablet pressing stage. In general, since the terahertz probes may be connected by fibres to the terahertz analysis equipment, they can be placed anywhere along the production line where it is necessary to monitor any of the above quantities or similar quantities.

Previously, much of the discussion has concentrated on the use of the present invention in relation to pharmaceutical analysis. However, as previously described, the present invention can be used for other types of samples. For example, to monitor paint thickness, uniformity and contaminants corrosion on car, aircraft and ship bodies. It can also be used for composite material inspection on aircraft, postal and package inspection, foodstuff and food product inspection etc.

Figure 10:
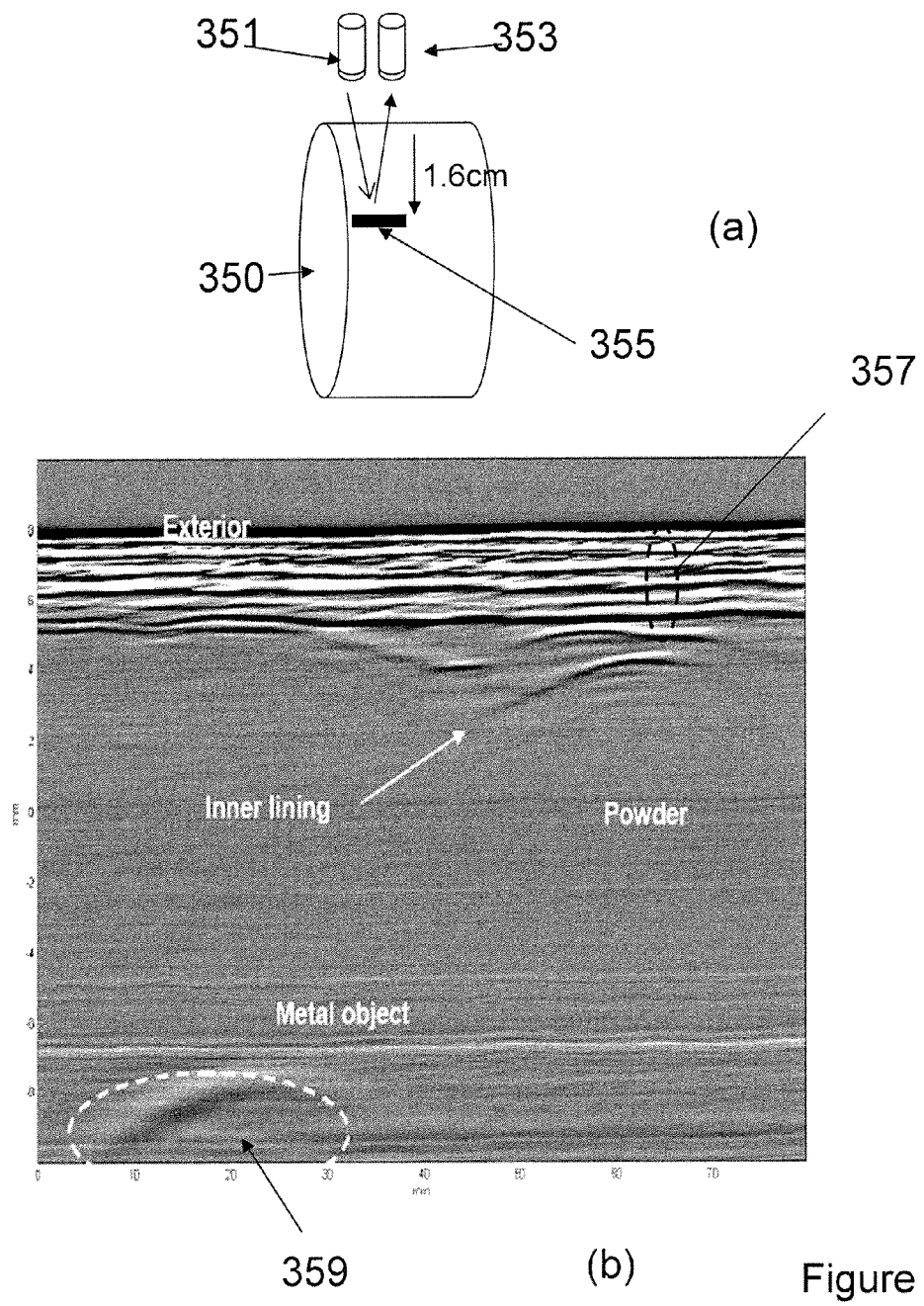
FIG. 10a is a schematic of a cardboard drum filled with powder and a metal object.
FIG. 10b is the corresponding THz depth profile of the drum.

FIG. 10 illustrates how terahertz radiation may be used to inspect a cardboard drum which is filled with powder and a metal object inside. FIG. 10a shows the drum 350 with a metal object 355 positioned 1.6 cms below a side. THz radiation is emitted by terahertz emitter 351 and detected by terahertz detector 353. Detector 353 may detect as spurious signal. Therefore, in quality control, the system is provided with either an optical system of the type described with reference to FIG. 7 or a software electronic distinguishing system as described with reference to FIG. 4.

FIG. 10b shows the results of an image taken using the system of FIG. 10a. The detail which the terahertz system may obtain concerning the laminated layers of the drum is shown as 357. The metal object 359. laying below the surface of the drum can be seen.

What is claimed is:

1. A system for investigating a plurality of samples having varying positions or orientations moving with respect to said system, the system comprising:

an emitter of terahertz radiation for irradiating a sample provided in a sample space;
a detector of terahertz radiation configured to detect radiation reflected from said sample space; and
an acquisition system configured to compare a received detector signal with a threshold of signal quality to determine if radiation reflected from said sample space is from a sample with a predetermined orientation in said sample space,
wherein the system is configured to use signals from a sample with said predetermined orientation to determine information about the composition of the sample.

2. A system according to claim 1, wherein said received detector signal is compared with a threshold by comparing the height of the received pulse with a threshold value for the height of the received pulse.

3. A system according to claim 1, wherein the height of the received pulse is the maximum height of the received pulse, the height of a pulse within a narrow time window or the height of a pulse with a pulse width below a maximum value.

4. A system according to claim 1, further comprising memory means configured to store received detector signals and said acquisition system is configured to sift through said signals in said memory means.

5. A system according to claim 1, further comprising a conveyor belt, chute or container configured to move said samples with respect to said sample space.

6. A system according to claim 1, wherein said emitter and said detector are housed in a hand held probe housing.

7. A system according to claim 1, wherein the detector performs the measurement in a time scale such that the sample motion introduces an error of 10% or less.

8. A system according to claim 1, further comprising a plurality of detectors configured to detect radiation from the sample space.

9. A system according to claim 1, further comprising a plurality of emitters.

10. A production line comprising:
manufacturing means comprising a plurality of stages for producing samples,
delivery means for moving samples to and from said stages; and
a system according to claim 1, coupled to said line for investigating samples moving on said delivery means.

11. A production line according to claim 10, wherein said delivery means comprise a conveyor belt, chute or container.

12. A method for investigating a plurality of samples having varying positions or orientations moving with respect to a system for investigating said sample, the method comprising:
irradiating with THz radiation a sample provided in a sample space;
detecting THz radiation reflected from said sample space;
comparing a received detector signal with a threshold of signal quality to determine if radiation reflected from said sample space is from a sample with a predetermined orientation in said sample space; and using signals from a sample with said predetermined orientation to determine information about the composition of said sample.

* * * * *